United States Patent [19]
Nara et al.

[11] Patent Number: 4,535,155
[45] Date of Patent: Aug. 13, 1985

[54] METHOD FOR SEPARATING CEPHALOSPORINS

[75] Inventors: Kiyoshi Nara, Kyoto; Kazuyoshi Katamoto, Suita; Kazuhiko Ohta, Ikeda, all of Japan

[73] Assignee: Takeda Chemical Industries, Ltd., Osaka, Japan

[21] Appl. No.: 522,549

[22] Filed: Aug. 11, 1983

Related U.S. Application Data

[63] Continuation of Ser. No. 220,727, Dec. 29, 1980, abandoned, which is a continuation-in-part of Ser. No. 74,808, Sep. 11, 1979, abandoned.

[30] Foreign Application Priority Data

Sep. 14, 1978 [JP]  Japan .................................. 53-113096

[51] Int. Cl.³ ............................................ C07D 501/12
[52] U.S. Cl. ...................................................... 544/20
[58] Field of Search ........................................... 544/20

[56] References Cited

U.S. PATENT DOCUMENTS 3,709,880  1/1973  Goegelman et al. ................. 544/20
3,926,973  12/1975  Nara et al. ............................ 544/20
3,983,108  9/1976  Pines .................................... 544/20

Primary Examiner—Glennon H. Hollrah
Assistant Examiner—James H. Turnipseed
Attorney, Agent, or Firm—Wenderoth, Lind & Ponack

[57] ABSTRACT

The interseparating of desacetyl-cephalosporin C, desacetoxy-cephalosporin C and cephalosporin C can be accomplished by adsorbing these available cephalosporins on activated carbon and effecting a fractional elution thereof with water containing 0 to 20 percent (V/V) of an organic solvent or solvents.

15 Claims, 1 Drawing Figure

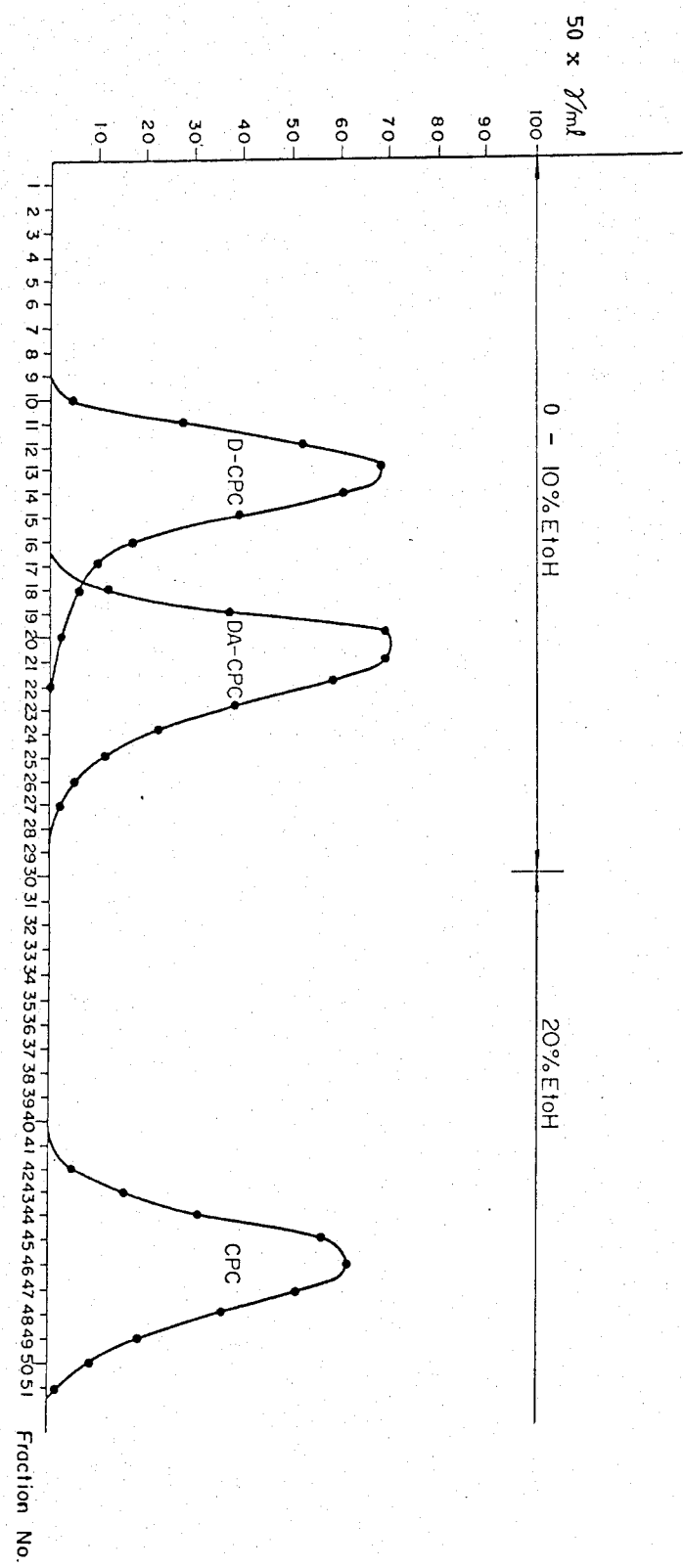

METHOD FOR SEPARATING CEPHALOSPORINS

This application is a continuation of application Ser. No. 220,727 filed Dec. 29, 1980 (now abandoned) which application is a continuation-in-part of Ser. No. 74,808 filed Sept. 11, 1979, now abandoned.

This invention relates to a method of separating the cephalosporin components of a cephalosporin mixture comprising at least two of the following cephalosporin compounds, namely desacetyl-cephalosporin C (hereinafter referred to briefly as D-CPC), desacetoxy-cephalosporin C (hereinafter, DA-CPC) or cephalosporin C (hereinafter, CPC).

D-CPC, DA-CPC and CPC, which have the structural formulas presented below, are all important intermediate compounds of value for the production of semi-synthetic cephalosporins.

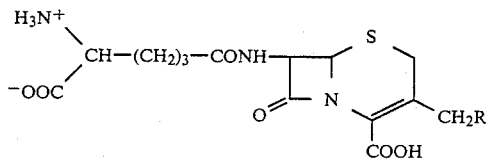

```
R: —OCOCH3 — CPC
 : —OH     — D-CPC
 : —H      — DA-CPC
```

It generally requires a complicated procedure to isolate CPC, D-CPC and DA-CPC severally from the fermentation broth of a microorganism which produces and accumulates concurrently two or more members of CPC, D-CPC and DA-CPC (such as the strains described in U.S. Pat. No. 3,979,260, Canadian patent 1,016,091, British Pat. No. 1,474,740, for instance). Thus, although the separation of these components has heretofore been carried out by cellulose column chromatography, a satisfactory separation can only be achieved when (1) the culture broth or filtrate is previously concentrated to as small a volume as possible, (2) a very large amount of cellulose is employed, and (3) a long time is expended for eluting through the large amount of cellulose and concentrating the obtained eluate. These and other disadvantages have made the conventional process using cellulose column chromatography unsatisfactory for commercial purposes. It has also been attempted to replace the cellulose with activated carbon for chromatographic runs (e.g. U.S. Pat. No. 3,926,973), but such process has been proposed only to separate CPC, cephalosporin N and pigment from each other and it is not known to us at all that activated carbon has even been employed for the interseparation of CPC, D-CPC and DA-CPC.

In some cases (e.g. U.S. Pat. No. 3,979,260, Canadian Pat. No. 1,016,091, British Pat. No. 1,474,740, etc.), activated carbon has been employed in a mere purification means for the purification of crude aqueous solutions containing two or more members of CPC, D-CPC and DA-CPC, but this adsorbent has never been utilized for the interseparation of cephalosporin derivatives.

The research undertaken to develop a method of separating a cephalosporin mixture into its components such as CPC, D-CPC and DA-CPC led us to the finding that a commercially ideal interseparation of D-CPC, DA-CPC and CPC can be accomplished by adsorbing these compounds on activated carbon and effecting a fractional elution thereof with water which may contain a small volume of an organic solvent or solvents. This invention has been developed on the basis of the above finding. This invention is therefore concerned with a method of separating severally such cephalosporin compounds by taking advantage of their differential affinity for activated carbon in water containing 0 to 20 percent (V/V) of an organic solvent or solvents. More particularly, the invention is concerned with a method of separating severally D-CPC, DA-CPC and CPC characterized by contacting a crude aqueous solution containing at least two members of CPC, D-CPC and DA-CPC with activated carbon to adsorb the cephalosporins on the carbon and effecting a fractional elution thereof with water containing 0 to 20 percent (V/V) of an organic solvent or solvents.

The crude aqueous solution of CPC, D-CPC and DA-CPC to which the method of this invention is applicable is a solution containing at least two members of CPC, D-CPC and DA-CPC, and may be any of cephalosporin fermentation broths and partially purified broths, e.g. eluates from ion exchange resins, concentrates, crystallization mother liquors and so forth. When D-CPC is present, it is particularly beneficial to apply the method of this invention to a partially purified solution containing certain salts. Thus, the adsorption on activated carbon is high when salts such as alkali metal or alkaline earth metal halide (e.g. sodium chloride, potassium chloride, magnesium chloride, etc.), alkali metal sulfate (e.g. sodium sulfate, etc.), alkali metal nitrate (e.g. sodium nitrate, etc.), alkali metal formate (e.g. sodium formate, etc.) alkali metal acetate (e.g. sodium acetate, etc.), alkali metal citrate (e.g. sodium citrate, etc.) and/or alkali metal phosphate (e.g. sodium phosphate, etc.) are concomitantly present in a proportion of 0.01 to 2 mols and, preferably, 0.05 to 0.5 mol.

The activated carbon which is employed for the purposes of this invention may be any of the activated carbons obtained by steam or chemical (e.g. zinc chloride) activation of saw dust carbon, coconut shell carbon, coal and other carbonaceous materials, although zinc chloride-activated carbons are particularly desirable. It is further desirable that such carbons are granular and have a size of 10 to 50 mesh.

In working this invention, said crude aqueous solution containing at least two members of CPC, D-CPC and DA-CPC is first contacted with activated carbon to thereby adsorb these solutes on the carbon.

When a column is employed for adsorption, it is advantageous to run the solution from the top of the column so that a better elution performance may be obtained. While the length of the column and the rate of contact should be properly selected, the contact rate is normally 0.1 to 2.0 SV (SV stands for space velocity which is defined as the ratio of the volume of inlet material to the volume of the reaction space, i.e. packed zone in the column, under standard conditions and per unit of time) and, preferably, within the range of 0.5 to 1.0.

The contemplated compounds, i.e. at least two members of CPC, D-CPC and DA-CPC, which have thus been adsorbed on the activated carbon, emerge from the column in the order of D-CPC, DA-CPC and CPC when eluted with an aqueous solution containing 0 to 20 percent (V/V) of an organic solvent (or when the organic solvent has a solubility below 20% (V/V) with respect to water, an aqueous solution containing the same solvent up to the saturation point at the maximum). The organic solvent may be practically any solvent that is soluble even to the slightest extent in water. However, from economic considerations, alcohols, preferably having 1 to 8 carbon atom(s), more preferably 1 to 6 carbon atoms (e.g. methanol, ethanol, propanol, isopropyl alcohol, butanol, isobutyl alcohol, amyl alcohol, isoamyl alcohol, cyclohexanol, etc.), ethers, preferably having 1 to 6 carbon atom(s) (e.g. dioxane, tetrahydrofuran, methyl ethyl ether, etc.), ketones, preferably having 1 to 6 carbon atom(s) (e.g. acetone, methyl ethyl ketone, diethyl ketone, etc.) esters, preferably having 1 to 12 carbon atom(s) (e.g. ethyl acetate, butyl acetate, etc.) and so on are advantageous. The organic solvent may be used as a mixture of the above solvents. Of these solvents, alcohols are the most desirable, methanol being the best. The simplest elution procedure is one in which the concentration of the solvent is not varied in the course of elution, although an elution procedure with a varied concentration of the solvent may also be employed. For example, when D-CPC has been adsorbed, it is advantageous to carry out a first elution with water as the solvent to recover a fraction containing D-CPC alone and, then, a second elution with an aqueous solution containing 0.1 to 20 percent (V/V) of an organic solvent. To ensure an improved separation efficiency, rechromatography and other procedures which are conventionally employed in the art of column chromatography can be utilized. The eluate is collected in aliquot fractions, and the fractions rich in each desired cephalosporin compound can be detected by a suitable detection procedure (e.g. thin layer chromatography, paper electrophoresis, high performance liquid chromatography, etc.).

The fractions containing the particular contemplated compound may be pooled, neutralized with a base such as NaOH, KOH or ammonia, concentrated, lyophilized, treated with a solvent or treated in other routine manners, to obtain the corresponding salt. The pool of fractions, or an aqueous solution of the corresponding salt derived therefrom may be also desalted with an ion exchange resin to obtain the free acid and then finally concentrated, precipitated by the addition of a solvent, lyophilized or otherwise purified by an established procedure to isolate the compound in the free form. Further, the fractions containing the contemplated compound may be directly contacted with an acylating agent, the resultant fat-soluble derivative being recovered by extraction with a solvent. The above-mentioned and other purification procedures may be used alone or in a suitable combination.

The following examples are intended to illustrate this invention in further detail and should by no means be construed as limiting the scope of the invention. In this specification, "g", "mg", "l", "ml", "cm", "W", "V", "M", "min.", "hr.", "diam.", "temp.", "r.p.m.", "HPLC", "TLC", "UV", "NMR" and "IR" are abbreviations of "gram", "milligram", "liter", "milliliter", "centimeter", "Weight", "Volume", "Mole", "minute", "hour", "diameter", "temperature", "rotations per minute", "High Performance Liquid Chromatography", "Thin Layer Chromatography", "Ultra-Violet ray spectrum", "Nuclear Magnetic Resonance spectrum" and "Infrared ray spectrum". Resins named "Amberlite" are products manufactured by Rohm & Haas Co. in U.S.A. As the chromatography grade activated carbon, there is used one manufactured by Takeda Chemical Industries, Ltd. in Japan.

EXAMPLE 1

In 250 l of sodium acetate buffer (pH 6.0, 0.2M) are dissolved 250 g each of CPC, DA-CPC and D-CPC, and the solution is passed through a column (25 cm in diam. × 163 cm in height) of 80 l chromatography grade activated carbon as previously suspended in water, at SV=1.0 (80 l/hr.)

The column is washed with 80 l of water, followed by passage of 240 l of 0–10% EtOH at SV=1.0 (80 l/hr.). The eluate is collected in 8 l fractions which are assayed by HPLC. The HPLC gives an elution curve corresponding to the first half of the attached drawing. It is clear that D-CPC and DA-CPC are eluted in two distinct patterns. A further amount of 10% EtOH may be passed to elute CPC but in order to save on the elution time and obtain a better-defined elution curve, the eluant is replaced with 20% EtOH and the eluate is collected in 8 l fractions. As assayed by HPLC, there is obtained an elution curve corresponding to the second half of the drawing. Each fraction is applied to a thin-layer chromatoplate of microcrystalline cellulose powder (Tokyo Kasei K.K. Japan) and the chromatogram is developed with n-butanol-acetic acid-water (3:1:1, V/V), and dried in air. The image formed by color-reaction with ninhydrin shows a spot each at Rf=0.15 for D-CPC, RF=0.28 for CPC and Rf=0.30 for DA-CPC.

Fractions No. 10–17, which are rich in D-CPC, are combined, adjusted to pH 6.5 with NaOH and concentrated under reduced pressure. To the resultant syrup is added ethanol to crystallize the D-CPC as the monosodium salt. The crystals are recovered by filtration and dried. By the above procedure is obtained 200 g of D-CPC.Na.3.5.H$_2$O. This product is found to be identical with an authentic sample of D-CPC.Na in physical, chemical and biological properties, e.g. antimicrobial spectrum, paper chromatography, TLC, UV, NMR and IR.

Then, fractions Nos. 18–28, which are rich in DA-CPC, are combined, adjusted to pH 6.5 with NaOH and concentrated under reduced pressure. To the resultant syrup is added ethanol, whereupon DA-CPC.Na salt is crystallized. The crystals are recovered by filtration and dried. By the above procedure is obtained 180 g of DA-CPC.Na salt. This product is found to be identical with an authentic sample of DA-CPC.Na salt in physical, chemical and biological properties, e.g. antimicrobial spectrum, paper chromatography, TLC, UV, IR and NMR.

Lastly, fractions Nos. 41–51, which are rich in CPC, are combined, adjusted to pH 6.5 with NaOH and the concentrated under reduced pressure. To the resultant syrup is added ethanol, whereupon CPC.Na salt separates out as crystals. The crystals are collected by filtration and dried. By the above procedure is obtained 150 g of CPC.Na.2H$_2$O. These crystals are found to be identical with an authentic sample of CPC.Na salt in physical, chemical and biological properties, e.g. antimicrobial spectrum, paper chromatography, TLC, UV, IR and NMR.

Five grams each of the obtained CPC, D-CPC and DA-CPC are taken and each dissolved in 50 ml of water. Columns each packed with 15 ml of Amberlite IR-120 (H+-form) are previously washed and cooled with cold water at 5° C. The above solutions are desalted by passage through the columns at SV=3–5 and each desalted solution is lyophilized. By the above procdure are obtained 3.2 g of CPC, 3.5 g of D-CPC and 3.3 g of DA-CPC.

EXAMPLE 2

250 ml of sodium citrate buffer (pH 8.0, 0.2M) containing 2,475 γ/ml of CPC and 2,200 γ/ml of D-CPC is passed through a column (2 cm in diam. ×32 cm in height) packed with 100 ml of chromatography grade activated carbon at SV=1.0 (100 ml/hr.) The column is rinsed with 100 ml of pure water and, then, 5% methanol is passed at SV=1.0 (100 ml/hr.), whereby 200 ml of a first eluate is obtained. The CPC and D-CPC contents of this first eluate are assayed by HPLC. The chromatogram shows that the eluate contains 523 mg (yield 95%) of D-CPC, with substantially no evidence of CPC. The above column is further irrigated with 5% methanol at SV=1.0 to collect 30 ml of a second fraction and, then, 30 ml of a third fraction. Then, 20% methanol is passed at SV=1.0 to obtain 340 ml of a fourth eluate. The third fraction (30 ml) obtained with 5% methanol is combined with the fourth fraction (340 ml) obtained with 20% methanol and the mixture is assayed by HPLC. The chromatogram shows the presence of 464 mg (yield 75%) of CPC, with substantially no evidence of D-CPC. The above fractions are respectively concentrated and crystallized as in Example 1 to recover 420 mg of D-CPC.Na.3.5.H$_2$O and 390 mg of CPC.Na.2H$_2$O.

EXAMPLE 3

436 ml of sodium acetate buffer (pH 7.0, 0.2M) containing 269 mg of CPC and 1,522 mg of D-CPC is passed through a column (2 cm in diam. ×64 cm in height) containing 200 ml of chromatography grade activated carbon as previously suspended in water, at SV=1.0 (200 ml/hr.), whereby the D-CPC and CPC are adsorbed. Then, 1% acetone at 10° C. is passed at SV=1.0, the eluate being collected in 50 ml fractions. Each of the fractions is assayed by TLC as in Example 1 and appropriate fractions (fractions Nos. 2–12 in this example) are combined and assayed by HPLC. The chromatogram shows the presence of 1,430 mg (yield 94%) of D-CPC, with substantially no evidence of CPC. Then, after fractions Nos. 14–24 are collected, 20% acetone is passed at SV=1.0 until the fraction No. 29 is obtained. The fractions Nos. 14–29 are combined and the D-CPC and CPC contents of the pool are assayed by HPLC. This chromatogram shows the presence of 172 mg (yield 63.9%) of CPC, with no evidence of D-CPC. These eluates are each crystallized as in Example 1 to recover 1.2 g of D-CPC.Na.3.5H$_2$O and 150 mg of CPC.Na.2H$_2$O.

EXAMPLE 4

441 ml of sodium acetate buffer (pH 7.0, 0.2M) containing 272 mg of CPC and 1,539 mg of D-CPC is chromatographed on a column (2 cm in diam. ×64 cm in height) of 200 ml of chromatography grade activated carbon as previously suspended in water, at SV=1.0 (200 ml/hr.), whereby the CPC and D-CPC are adsorbed. After the column is rinsed with 200 ml of pure water, 1% ethyl acetate at 10° C. is passed at SV=1.0, the eluate being collected in 50 ml fractions. Each of the fractions is assayed by TLC, appropriate fractions are combined and the D-CPC and CPC contents of the pool are assayed by HPLC. The fractions Nos. 2–18 contain 1,462 mg (yield 95%) of D-CPC, with substantially no evidence of CPC. The fractions Nos. 20–25 are found to contain 233 mg (yield 85.6%) of CPC, with substantially no evidence of D-CPC.

EXAMPLE 5

447 ml of sodium acetate buffer (pH 7.0, 0.2M) containing 275 mg of CPC and 1,560 mg of D-CPC is passed through a column packed with 200 ml of chromatography grade activated carbon as previously suspended in water, at SV=1.0 (200 ml/hr.), whereby the CPC and D-CPC are adsorbed. After the column is rinsed with 200 ml of pure water, 0.1% tetrahydrofuran at 10° C. is passed at SV=1.0, the eluate being collected in 50 ml fractions. The fractions Nos. 1–15 contain a total of 1,443 mg of D-CPC (yield 92.5%), with substantially no evidence of CPC. Then, 250 ml of 0.5% tetrahydrofuran at 10° C. is passed at SV=1.0, followed by passage of 1% tetrahydrofuran at 10° C., again at SV=1.0. The fractions Nos. 21–33 are combined and assayed by HPLC. The chromatogram shows the presence of 213.2 mg of CPC (yield 78%), with substantially no evidence of D-CPC.

EXAMPLE 6

250 ml of sodium formate buffer (pH 6.0, 0.2M) containing 1,125 mg of CPC and 1,075 mg of D-CPC is passed through a column of 200 ml of chromatography grade activated carbon as previously suspended in water, at SV=1.0 (200 ml/hr.), whereby the CPC and D-CPC are adsorbed. The column is rinsed with 200 ml of pure water. Then, 800 ml of water at 10° C. is passed at SV=1.0 (200 ml/hr.), the eluate being collected in 50 ml fractions. Then, 1,100 ml of 20% methanol is passed at SV=1.0. The fractions Nos. 5–16 contain 908 mg of D-CPC (yield 84%), with substantially no evidence of CPC. The fractions Nos. 18'38 contain 825 mg of CPC (yield 73%), with substantially no evidence of D-CPC.

EXAMPLE 7

A 2-liter Sakaguchi flask is filled with 500 ml of a seed culture medium composed of 3.0% sucrose, 1.5% meat extract, 0.5% corn steep liquor and 0.15% CaCO$_3$, and inoculated with *Cephalosporium acremonium* ATCC 14553. The inoculated flask is incubated on a reciprocating shaker at 28° C. for 3 days. On the other hand, a 50-liter fermentation tank of stainless steel is charged with 30 l of a medium composed of 3.0% sucrose, 3.2% raw soybean flour, 0.5% DL-methionine and 0.15% CaCO$_3$, sterilized in the routine manner and cooled. The tank medium is aseptically inoculated with the above seed culture, and fermentation under agitation and aeration is carried out at 28° C. (aeration 100%/min.; 200 r.p.m.). After 120 hours of fermentation, the broth is withdrawn and filtered. The CPC and D-CPC contents of the filtrate are assayed by HPLC. The results are 135 γ/ml of CPC and 25 γ/ml of D-CPC. To 25.7 l of this filtrate is added penicillinase (Schwarz-Mann Co., Ltd.), whereby the cephalosporin N is completely decomposed. The solution is adjusted to pH 4.0 with dilute sulfuric acid, the insolubles are filtered off and the filtrate is cooled to 10° C. and chromatographed on a column (10 cm in diam. ×64 cm in height) of 5 l of chromatography grade activated carbon as previously suspended in water. The column is rinsed with 5 l of pure water. Then, elution is carried out with 40% aqueous acetone at 10° C. and 15 l of the eluate is cooled to 10° C. and passed through a column (3 cm in diam. ×71 cm in height) containing 500 ml of Amberlite IRA-402 (acetate-form), whereby the D-CPC and CPC are adsorbed. The column is rinsed with 2 l of pure water and, then, elution is carried out with 2.5 l of 0.2M sodium acetate buffer (10° C., pH 7.0) at SV=1.0 (500 ml/hr.)

This eluate is passed through a column (2 cm in diam.×127 cm in height) containing 400 ml of chromatography grade activated carbon as previously suspended in water, at SV=1.0 (400 ml/hr.), followed by rinsing with 400 ml of pure water. Then, 1% methanol at 10° C. is passed at SV=1.0, the eluate being collected in 100 ml fractions. The fractions Nos. 5–11 are pooled, and TLC on microcrystalline cellulose is carried out with a solvent system of n-butanol-acetic acid-water (3:1:1). The chromatogram shows a single spot substantially corresponding to D-CPC alone at Rf=0.15, with almost no evidence of CPC. The same column is further eluted with 20% methanol at SV=1.0 and appropriate fractions (Nos. 12–32 in this case) are combined and assayed by TLC under the same conditions as above. The chromatogram shows a single spot substantially corresponding to CPC alone at Rf=0.28, with no evidence of D-CPC. The above pool of D-CPC fractions (Nos. 5–11) is neutralized with NaOH and concentrated under reduced pressure (internal temp.≦20° C.) until the free acid of D-CPC is 25 to 30% (W/V). To this concentrate is added ethanol, whereby crystals are formed. After allowing the system to crysallize at 5° C. overnight, the crystals are collected by filtration and dried. Pale yellow crystals of D-CPC.Na salt are thus obtained. Repeated crystallization from the mother fluid yields a total of 60 mg of D-CPC.Na salt. These crude crystals are further purified and the resultant D-CPC.Na salt crystals are compared with an authentic sample of D-CPC.Na salt. The physical, chemical and biological properties of this product are in good agreement with those of the authentic sample of D-CPC.Na salt. Then, CPC fractions (Nos. 12–32) are neutralized with NaOH and treated as described above with reference to D-CPC, whereby CPC is precipitated. This procedure yields a total of 240 mg of CPC.Na salt powder. This is further purified and compared with an authentic sample of CPC.Na salt. There is a good agreement in physical, chemical and biological properties.

EXAMPLE 8

*Cephalosporium acremonium* K-121 (ATCC 20427) is precultured as in Example 7. On the other hand, a 50-liter fermentation tank of stainless steel is charged with 30 l of a medium composed of 6.0% sucrose, 5.0% glucose, 3.0% peanut cake, 1.0% DL-methionine and 0.15% $CaCO_3$, sterilized in the routine manner and cooled. The tank is aseptically inoculated with the above seed culture and fermentation under agitation and aeration is conducted at 28° C. for 190 hours (aeration 100%/min.; agitation at 250 r.p.m.). At the end of the incubation period, the broth is withdrawn and the solid matter is removed to obtain 25 l of filtrate. The CPC content of this filtrate is 10500 γ/ml. To this filtrate is added the D-CPC obtained by the procedure of U.S. Pat. No. 3,926,729 to a concentration of 1000 γ/ml.

Twenty-five liters of the above filtrate containing 10500 γ/ml of CPC and 1000 γ/ml of D-CPC is cooled to 10° C. and passed serially through a column of 2.8 l of Amberlite IRC-50 ($H^+$-form) and a column of 17.8 l of Amberlite IRA-402 ($CH_3COO^-$-form) at the rate of 17.8 l/hr., whereby the D-CPC and CPC are adsorbed. The columns are serially rinsed with 70 l of pure water at 10° C. and the Amberlite IRA-402 column is eluted with sodium acetate buffer at 10° C. (pH 7.5, 0.2M) at the rate of 17.8 l/hr. to recover 89 l of eluate (pH 7.5). This eluate is chromatographed on a column (14 cm in diam.×136 cm in height) of 21 l of chromatography grade activated carbon as previously suspended in water, at 10° C. and at the flow rate of 10 l/hr., whereby the CPC and D-CPC are adsorbed. The column is rinsed with 21 l of water and elution is carried out with 58 l of 1% aqueous methanol at 10° C. for an hour, at the flow rate of 10 l/hr., the eluate being collected in 5.3 l fractions. Then, 110 l of 20% aqueous methanol at 10° C. is passed at the flow rate of 10 l/hr., the eluate being collected in 5.3 l fractions.

Each fraction is assayed by TLC and the fraction Nos. 5–11 which give a single spot of D-CPC at Rf=0.15 and the fraction Nos. 12–32 which give a single spot of CPC at Rf=0.28 are respectively combined. The D-CPC fractions, i.e. fraction Nos. 5–11, are neutralized with NaOH and, then, concentrated and crystallized as in Example 1 to recover a total of 15 g of D-CPC.Na salt crystals. The CPC fractions, i.e. fraction Nos. 12–32, are similarly neutralized, concentrated and crystallized as in Example 1 to recover a total of 135 g of CPC.Na salt crystals.

EXAMPLE 9

In accordance with the procedure described in Example 7, *Cephalosporium acremonium* K-121 (ATCC 20427) is incubated for 96 hours. At the end of the incubation period, the fermentation broth is withdrawn and the solid matter is removed to obtain 26.5 l of filtrate. The CPC content of this filtrate is 4700 γ/ml. To this filtrate is added the D-CPC prepared by the procedure of U.S. Pat. No. 3,926,728 to a concentration of 5000 γ/ml.

Then, 26.5 l of the above filtrate containing 4700 γ/ml of CPC and 5000 γ/ml of D-CPC is cooled to 10° C. and passed serially through a column of 2.5 l of Amberlite IRC-50($H^+$-form) and a column of Amberlite IRA-402 ($CH_3COO^-$-form) at the flow rate of 16 l/hr., whereby the CPC and D-CPC are adsorbed. The columns are then serially rinsed with 64 l of pure water at 10° C. and eluation is carried out on the Amberlite IRA-402 column with sodium acetate buffer (pH 7.0, 0.2M, 10° C.) at the flow rate of 16 l/hr. to recover 80 l of eluate (pH 7.0).

This eluate is passed through a column (14 cm in diam.×136 cm in height) of 19 l of chromatography grade activated carbon as previously suspended in water, at the flow rate of 10 l/hr., whereby the CPC and D-CPC are adsorbed. The column is rinsed with 19 l of cold water and, then, water at 10° C. is further passed at 19 l/hr., whereby 42.8 l of a colorless, clear eluate is obtained. The TLC of this eluate gives substantially a single spot of D-CPC. Then, 33.3 l of 3% ethanol at 10° C. is passed, and after 9.5 l of forerun fractions are separated, 23.8 l of after-run fractions are pooled. The latter contains CPC only. Then, 57 l of 15% aqueous ethanol at 10° C. is passed at the flow rate of 19 l/hr. and the eluate is combined with the above 23.8 l eluate (3% aqueous ethanol). The assay of this combined eluate (80.8 l) by HPLC showed the presence of 86 g of CPC, with substantially no evidence of D-CPC.

The D-CPC and CPC fractions thus obtained are independently concentrated and crystallized as in Example 1 to recover 80 g of D-CPC.Na salt crystals and 66 g of CPC.Na salt crystals.

EXAMPLE 10

By the procedure described in Example 7, *Cephalosporium acremonium* K-121 (ATCC 20427) is incubated for 48 hours. At the end of the incubation period, the broth is withdrawn and the solid matter is removed to obtain 27.2 l of filtrate. The CPC content of this filtrate is 1020 γ/ml. To this filtrate is added the D-CPC obtained by the procedure of U.S. Pat. No. 3,926,729 to a concentration of 9000 γ/ml.

27.2 l of the above filtrate containing 1020 γ/ml of CPC and 9000 γ/ml of D-CPC is cooled to 10° C. and passed serially through a column of 2.7 l of Amberlite IRC-50 (H+-form) and a column of 17 l of Amberlite IRA-410 ($CH_3COO^-$-form) at a flow rate of 17 l/hr., whereby the CPC and D-CPC are adsorbed. After rinsing with 68 l of cold water, elution is carried out on the Amberlite IRA-410 column with sodium acetate buffer (pH 7.0, 0.2M, 10° C.) at a flow rate of 17 l/hr. to recover 85 l of eluate (pH 7.0). This eluate is chromatographed on a column (14 cm in diam.×130 cm in height) of 20 l of chromatography grade activated carbon as previously suspended in water, at a flow rate of 20 l/hr., whereby the CPC and D-CPC are adsorbed. After rinsing with 20 l of cold water, elution is carried out with 75 ml of 1% aqueous isopropyl alcohol at 10° C. and at a flow rate of 20 l/hr. The assay of this eluate (75 l) by HPLC reveals the presence of 204 g of D-CPC in this eluate (75 l), with substantially no evidence of CPC. Then, 5% aqueous isopropyl alcohol is passed at 20 l/hr., and after 10 l of the forerun fractions have been discarded, 60 l is further passed to obtain a pale yellow, clear eluate. The assay of this eluate revealed the presence of 12 g of CPC. These D-CPC and CPC fractions are independently concentrated and crystallized to recover 190 g of D-CPC.Na salt crystals and 6 g of CPC.Na salt crystals.

EXAMPLE 11

A 2-liter Sakaguchi flask is filled with 500 ml of a medium composed of 5% glucose, 1% cotton seed flour, 0.5% raw soybean flour, 0.5% yeast extract, 0.5% peptone and 1% $CaCO_3$, and after sterilization, inoculated with *Paecilomyces carneus* C-2237 (IFO 9729). The inoculated flask is incubated on a reciprocating shaker at 28° C. for 3 days. On the other hand, a 50 l fermentation tank of stainless steel is charged with 30 l of a medium composed of 8% glucose, 2% cotton-seed flour and 1% $CaCO_3$, sterilized in the routine manner and cooled. This tank is aseptically inoculated with the culture prepared above and fermentation under agitation and aeration is carried out at 24° C. for 164 hours (aeration 20 l/min., agitation 230 r.p.m.).

At the end of the fermentation period, the fermentation broth is withdrawn and the solid matter is removed to obtain 25 l of filtrate. This filtrate contains 110 γ/ml of CPC, 30 γ/ml of D-CPC and 155 γ/ml of DA-CPC. To this broth is added penicillinase (Schwarz-Mann Co., Ltd.) to completely decompose the cephalosporin N and after it has been adjusted to pH 4.0 with dilute sulfuric acid, the insolubles are filtered off. The filtrate is cooled to 5° C. and chromatographed on a column (10 cm in diam.×64 cm in height) of 5.0 l of chromatography grade activated carbon as previously suspended in water. After rinsing with cold water, elution is carried out with 50% aqueous acetone at 5° C. The eluate (15 l, pH 5.0) is cooled to 10° C. and chromatographed on a column of 3.5 l of Amberlite IRA-410 ($Cl^-$-form), whereby the CPC, D-CPC and DA-CPC are adsorbed. After rinsing, elution is carried out with 10 l of 0.2M sodium chloride solution at 5° C. and at SV=1.0 (3.5 l/hr.). This eluate is passed through a column (5 cm in diam.×300 cm in height) of 6 l of chromatography grade activated carbon as previously suspended in water, at SV=1.0 (6 l/hr.). After rinsing, 5% aqueous methanol at 5° C. is passed at SV=1.0 (6 l/hr.), the eluate being collected in 1.2 l fractions. The fractions are assayed by TLC. It is found that D-CPC emerges first, followed by DA-CPC. After DA-CPC has been completely eluted, 20% aqueous methanol is further passed at SV=1.0 (6 l/hr.), whereupon CPC emerges finally. The fractions rich in D-CPC (fractions Nos. 6-10) are combined, neutralized with NaOH, concentrated and crystallized to obtain a total of 35 mg of D-CPC.Na salt. Then, fractions Nos. 11-17 which are rich in DA-CPC are combined, neutralized with NaOH, concentrated, crystallized and dried, whereupon 380 mg of DA-CPC.Na salt is obtained. Fractions Nos. 22-40, which are rich in CPC, are combined, neutralized with NaOH, concentrated and crystallized to recover 130 mg of CPC.Na salt.

EXAMPLE 12

A 2-liter Sakaguchi flask is filled with 500 ml of a medium composed of 5% sucrose, 1% cotton seed flour, 3% corn steep liquor and 0.15% $CaCO_3$ and after sterilization, is inoculated with *Anixiepsis peruviana* BS-301.67. The inoculated flask is incubated on a reciprocating shaker at 28° C. for 4 days. On the other hand, a 50-liter fermentation tank of stainless steel is charged with 30 l of a medium composed of 8% glucose, 2% cotton seed flour, 1% raw soybean flour, 1% corn steep liquor, 0.5% DL-methionine and 1% $CaCO_3$, sterilized in the routine manner and cooled. This tank medium is aseptically inoculated with the preculture obtained above and fermentation under agitation and aeration is carried out at 28° C. (aeration 100%; agitation 280 r.p.m.). After 184 hours of incubation, the culture broth is withdrawn and the solid matter is removed, whereby 25 l of filtrate is obtained. This filtrate contains 30 γ/ml of CPC, 110 γ/ml of D-CPC and 415 γ/ml of DA-CPC.

To this filtrate is added penicillinase (Schwarz-Mann Co., Ltd.) to completely decompose the cephalosporin N, and after adjustment to pH 4.0 with dilute sulfuric acid, the insolubles are filtered off. The filtrate is cooled to 5° C. and chromatographed on a column (10 cm in diam.×64 cm in height) of 5 l of chromatography grade activated carbon as previously suspended in water. The column is washed with cold water and, then, elution is carried out with 40% aqueous acetone. The eluate (15 l, pH 5.0) is further passed through a column of 2 l of Amberlite IRA-402 ($CH_3COO^-$-form), whereby the CPC, D-CPC and DA-CPC are adsorbed. After rinsing, elution is carried out with 10 l of 0.2M-sodium acetate buffer (pH 7.0, 5° C.) at SV=1.0 (2 l/hr.).

This eluate is chromatographed on a column (6 cm in diam.×208 cm in height) of 6 l of chromatography grade activated carbon as previously suspended in water at SV=1.0 (6 l/hr.) and, then, the column is rinsed with 8 l of cold water. After this rinsing, 1% isopropyl alcohol (5° C.) is passed at SV=1.0, the eluate being collected in 1.2 l fractions. As found by a TLC assay of the fractions, D-CPC emerges first, followed by the emergence of DA-CPC. After DA-CPC has been completely eluted, 5% aqueous isopropyl alcohol (5° C.) is passed at SV=1.0, whereupon CPC emerges.

The fractions rich in D-CPC, i.e. fraction Nos. 5–10, are pooled, adjusted to pH 6.5 with NaOH, concentrated and crystallized, whereby 200 mg of D-CPC.Na salt is obtained. Then, the fractions rich in DA-CPC, i.e. fraction Nos. 11–19, are pooled, adjusted to pH 6.5 with NaOH, concentrated and crystallized to recover DA-CPC.Na salt. The fractions rich in CPC, i.e. fraction Nos. 24–43 are pooled, adjusted to pH 6.5 with NaOH, concentrated and crystallized, whereby 40 mg of CPC.Na salt is obtained.

EXAMPLE 13

By the procedure described in Example 7, *Cephalosporium acremonium* K-121 (ATCC 20427) is cultivated for 96 hours. Thereafter, the fermentation broth is withdrawn and the solid matter is removed to recover 25 l of filtrate. This filtrate contains 4500 $\gamma$/ml of CPC. To this filtrate is added the D-CPC prepared by the method described in U.S. Pat. No. 3,926,729 to a concentration of 5000 $\gamma$/ml, followed by addition of the DA-CPC prepared by catalyst hydrogenation of CPC to a concentration of 5000 $\gamma$/ml.

The above filtrate (25 l) containing 4500 $\gamma$/ml of CPC, 5000 $\gamma$/ml of D-CPC and 5000 $\gamma$/ml of DA-CPC is cooled to 5° C. and passed serially through a column of 3.6 l Amberlite IRC-50 ($H^+$-form) and a column of 22 l Amberlite IRA-402 ($CH_3COO^-$-form) at the flow rate of 22 l/hr. The columns are then rinsed with 88 l of cold water in series. Thereafter, sodium acetate buffer (pH 7.0, 0.2M) at 5° C. is passed through the Amberlite IRA-402 column at 22 l/hr. to recover 110 l of eluate (pH 7.0). This eluate is passed through a column (10 cm in diam.×343 cm in height) of chromatography grade activated carbon as previously suspended in water, at 27 l/hr. whereby the CPC, D-CPC and DA-CPC are adsorbed. The column is rinsed with 27 l of cold water, followed by passage of 40 l of cold water (5° C.) at 27 l/hr., the eluate being collected in 2.7 l fractions. TLC assay of the eluate shows that D-CPC emerges first from the column. Then, 5% aqueous methanol is passed through the column, whereupon DA-CPC is eluted. After a thorough elution of DA-CPC, 20% aqueous methanol is further passed through the column at 27 l/hr., whereby CPC is recovered.

Fractions Nos. 5–25, which are rich in D-CPC, are combined, adjusted to pH 6.5 with NaOH, concentrated and crystallized to recover 50 g of D-CPC.Na salt. Then, fractions Nos. 26–43, which are rich in DA-CPC, are combined, adjusted to pH 6.5 with NaOH, concentrated and crystallized to recover 45 g of DA-CPC.Na salt. Finally, fractions Nos. 47–75, which are rich in CPC, are combined, adjusted to pH 6.5 with NaOH, concentrated and crystallized to obtain 30 g of CPC.Na salt.

What we claim is:

1. A method for isolating at least two members selected from the group consisting of cephalosporin C, desacetylcephalosporin C and desacetoxy-cephalosporin C from each other as contained in a crude aqueous solution of said members, which comprises contacting the crude aqueous solution with activated carbon to adsorb the said members in the solution on the carbon, and eluting the adsorbed members fractionally with water containing 0 to 20 percent (V/V) of an organic solvent or a mixture of organic solvents in the order of:
   desacetyl-cephalosporin C if present;
   desacetoxy-cephalosporin C if present;
   cephalosporin C if present.

2. A method according to claim 1, wherein the crude aqueous solution contains desacetyl-cephalosporin C.

3. A method according to claim 1, wherein the elution is conducted only with water.

4. A method according to claim 1, wherein the organic solvent is an alcohol, ether, ketone or ester.

5. A method according to claim 4, wherein the organic solvent is selected from the group consisting of alcohols of 1 to 8 carbon atoms, ethers of 1 to 6 carbon atoms, ketones of 1 to 6 carbon atoms and esters of 1 to 12 carbon atoms.

6. A method according to claim 2, wherein the alcohol is a $C_{1-6}$ alcohol.

7. A method according to claim 5, wherein the $C_{1-8}$ alcohol is methanol.

8. A method according to claim 1, wherein the eluent used in carrying out the fractional elution consists only of water, or is a mixture consisting only of water and up to 20 percent (V/V) of at least one organic solvent.

9. A method for isolating cephalosporin C, desacetyl-cephalosporin C and desacetoxy-cephalosporin C from each other as contained in a crude aqueous solution of said members, which comprises contacting the crude aqueous solution with activated carbon to adsorb the said members in the solution on the carbon, eluting the adsorbed members fractionally with water containing 0 to 20 percent (V/V) of an organic solvent or a mixture of organic solvents in the order of:
   desacetyl-cephalosporin C;
   desacetoxy-cephalosporin C;
   cephalosporin C, and recovering desacetyl-cephalosporin C, desacetoxy-cephalosporin C and cephalosporin C from the eluate in fractions.

10. A method according to claim 9, wherein the elution is conducted only with water.

11. A method according to claim 9, wherein the organic solvent is an alcohol, ether, ketone or ester.

12. A method according to claim 11, wherein the organic solvent is selected from the group consisting of alcohols of 1 to 8 carbon atoms, ethers of 1 to 6 carbon atoms, ketones of 1 to 6 carbon atoms and esters of 1 to 12 carbon atoms.

13. A method according to claim 12, wherein the alcohol is a $C_{1-6}$ alcohol.

14. A method according to claim 13, wherein the $C_{1-6}$ alcohol is methanol.

15. A method according to claim 9, wherein the eluent used in carrying out the fractional elution consists only of water, or is a mixture consisting only of water and up to 20 percent (V/V) of at least one organic solvent.

* * * * *